Figure 1:
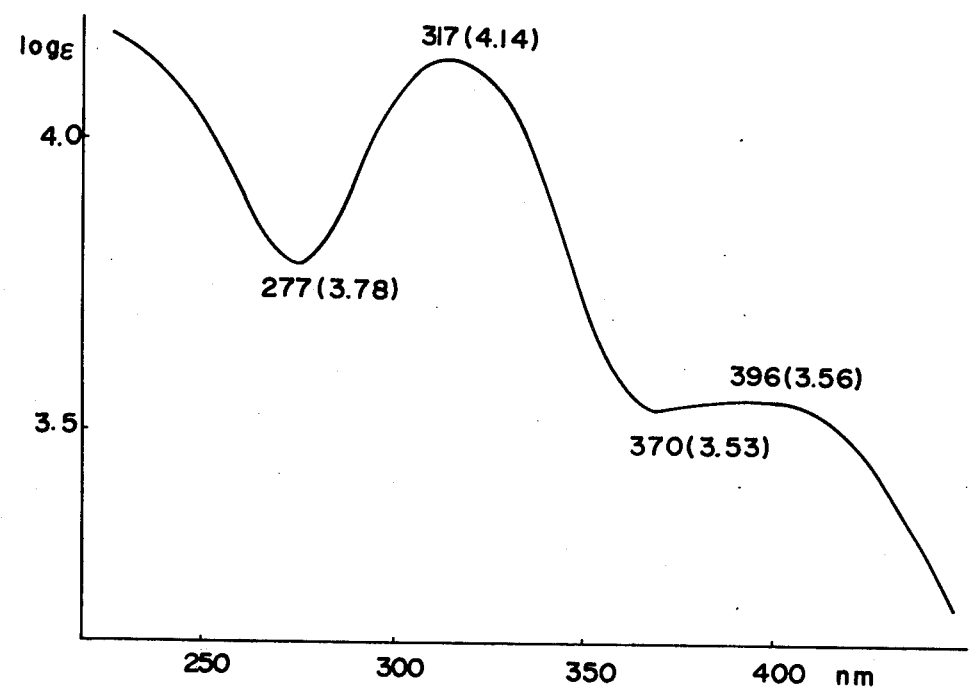

United States Patent [19] [11] 4,127,446
Arai [45] *Nov. 28, 1978

[54] PROCESS FOR PRODUCING ANTIBIOTICS MIMOSAMYCIN AND CHLOROCARCINS A, B AND C

[76] Inventor: Tadashi Arai, Kojimachi Sanbancho Kondo 401, 3-2, Sanbancho, Chiyoda-ku, Tokyo, Japan

[*] Notice: The portion of the term of this patent subsequent to Mar. 28, 1995, has been disclaimed.

[21] Appl. No.: 788,697

[22] Filed: Apr. 18, 1977

Related U.S. Application Data

[62] Division of Ser. No. 720,823, Sep. 7, 1975, abandoned.

[30] Foreign Application Priority Data

Sep. 19, 1975 [JP] Japan .................................. 50-113289

[51] Int. Cl.$^2$ ............................................... C12D 9/14
[52] U.S. Cl. .................... 195/80 R; 424/121; 424/118
[58] Field of Search ....................................... 195/80 R

[56] References Cited
PUBLICATIONS

The Journal of Antibiotics, vol. XXIX, No. 4, pp. 398–414, Apr. 1976.

Primary Examiner—Alvin E. Tanenholtz
Attorney, Agent, or Firm—Flynn & Frishauf

[57] ABSTRACT

Antibiotic substances; mimosamycin having antibacterial activities and chlorocarcins A, B and C having antitumor activities, and these antibiotics are produced by cultivation of *Streptomyces lavendulae* strain No. 314.

3 Claims, 12 Drawing Figures

PROCESS FOR PRODUCING ANTIBIOTICS MIMOSAMYCIN AND CHLOROCARCINS A, B AND C

This is a division, of application Ser. No. 720,823, filed Sept. 7, 1975 and now abandoned.

This invention relates to new antibiotic substances, mimosamycin and chlorocarcins A, B and C, as well as a process for producing the same.

More particularly, it is concerned with a new antibiotic named mimosamycin having antibacterial activities against gram-positive bacteria, especially acid-fast bacteria and three new antibiotics named chlorocarcins A, B and C and acid addition salts thereof. It is also concerned with a process for the production of antibiotic substances, mimosamycin and chlorocarcins A, B and C and acid addition salts thereof which comprises cultivating *Streptomyces lavendulae* strain No. 314, recovering a complex of chlorocarcins and mimosamycin from a cultured broth and then isolating mimosamycin and chlorocarcins A, B and C from said complex of chlorocarcins. Still more particularly, it is concerned with a process for the production of mimosamycin which comprises cultivating *Streptomyces lavendulae* strain No. 314 and recovering mimosamycin from a cultured broth, as well as with a process for the production of chlorocarcins A, B and C as well as an acid addition salt thereof which comprises cultivating *Streptomyces lavendulae* strain No. 314, recovering a complex of chlorocarcins from a cultured broth and then isolating said complex of chlorocarcins into chlorocarcins A, B and C.

Heretofore, isolation of about 2,000 different types of antibiotic substances has been reported and it has become difficult in the art to find out a new antibiotic substance. However, a new antibiotic substance has been increasingly needed due to appearance of those microorganisms resistant to conventional antibiotics as well as manifestation of new infectious diseases caused by a widespread application of antibiotics having a broad antibacterial spectrum, steroidal hormones, antitumor agents or antiimmune substances.

I has made studies for a process for the remarkably high production of antibiotic substances, which are produced and co-existing in a minor amount by a known antibiotic substance-producing microorganism, by improving a culture condition. As a result of his studies, it has been found that the actinomycetes capable of producing a known antibiotic streptothricin can also produce new and useful antibiotic substances, chlorocarcins A, B and C and mimosamycin, and also that *Streptomyces lavendulae* strain No. 314 can particularly produce high activity units of these new antibiotic substances.

It is an object of this invention to provide new antibiotics, mimosamycin and chlorocarcins A, B and C which show valuable biological activities.

Another object of this invention is to provide a process of the fermentative production of new antibiotics.

These and other objects will become apparent from the following description.

*Streptomyces lavendulae* strain No. 314 in this invention was isolated from a soil sample collected at Kyoto and belongs to the genus Streptomyces. This strain has been deposited under the accession No. 3218 with Technical Research Institute of Microbial Industry, Agency of Industrial Science & Technology, Ministry of International Trade and Industry, Japan, and also as NRRL-11002 in the Northern Regional Research Laboratory, Northern Central Region, Agricultural Research Service, United States Department of Agriculture, at Peoria, Illinois, U.S.A.

Observation of aerial mycelium and spore of *Streptomyces lavendulae* strain No. 314 was effected by cultivating the strain on the media according to the recommendations of the International Streptomyces Project (ISP) (Shirling. E. B. & D. Gottlieb; International *J. Systematic Bacteriol.* 16, 313–340, 1966); namely, by cultivating on agar plates of yeast-starch-agar medium, inorganic salts-starch-agar medium and maltose-containing basal medium for carbon source utilization pattern (Pridham-Gottlieb's agar medium) at 27° C. for 1–2 weeks. Also, colors of mycelium with mature spores, vegetative mycelium and others were determined according to the color chip number as taught in "Descriptive Color Name Dictionary", Container's Corporation of America, 1950 and "Color Harmony Manual", Container's Corporation of America, 1958.

The strain No. 314 develops wave-shaped folded aerial mycelium long-branched in a diameter of about 0.6°–1.0 $\mu$ with many cylindrical spores. Spores are 0.6–1.0 $\mu$ × 0.8–2.0 $\mu$ in size. According to the standard in ISP, the strain having the above morphological characteristics is said to belong to the Section Rectiflexibiles. However, the aerial hyphae are with loops or incomplete or elongated spirals which are in coils of 1–2 turns. Therefore, the strain No. 314 has been morphologically determined to belong to the Section Retinaculiaperti. When spore surface on these media are observed under electron microscope, the spore of the strain has been found to have a smooth surface. The strain No. 314 has main characteristics in that the aerial hyphae are morphologically of the Section Retinaculiaperti, color of the aerial hyphae with mature spores is rose to lavender on various media, color of the vegetative mycelium is sometimes blue to bluish brown on a synthetic medium and production of melanin pigment is positive. Then, searching the strains of the genus Streptomyces which are described in "The Actinomycetes", S. A. Waksman, Vol. 2, 1959 and "Bergey's Determinative Bacteriology", 8th Ed., 1974, it has been suspected that the strain has close resemblance to *Streptomyces lavendulae*. The strain No. 314 is inoculated to a conventional medium for producing an antibiotic substance and shaken culture is effected at 27° C. for a cultivation period of 18 to 72 hours to produce a culture filtrate having a high activity against coliform bacilli. The filtrate thus obtained is treated with active charcoal under alkaline condition, eluted with acidic acetone or adsorbed on a weak cation exchange resin, for example, Amberite IRC-50 (trade name, available from Rohm & Haas Co., U.S.A.) and subjected to desorption with 0.1 N hydrochloric acid to afford an antibacterial substance against coliform bacilli. Then, the substance thus obtained is purified by chromatography over, for example, Amberite CG-50 (trade name, available from Rohm & Haas Co.) and crystallized in the form of its Reinecke's salt or picrate, whereupon this substance is identified as streptothricin.

Further, comparison of cultural and physiological characteristics was made by the use of *Streptomyces lavendulae* IFM 1031, which is a streptothricin-producing strain, *Streptomyces racemochromogenes* IFM 1081, which is considered to be identical with *Streptomyces lavendulae* and capable of producing streptothricin, and the present strain for final identification. The results are summarized in Tables 1, 2 and 3. More specifically, the strain No. 314 has been identical with *Streptomyces lavendulae* in every characteristic property which is presently applied for identification of the strain in the genus Streptomyces, though minor differences are observed in some respects, for example, utilization of L-arabinose and the like, and thus the strain has been identified as *Streptomyces lavendulae*. Also, *Streptomyces racemochromogenes* can produce streptothricin, but this strain is apparently different from the strain No. 314 which is *Streptomyces lavendulae* from the above-mentioned comparison results.

Table 1

Comparison of Streptomyces strain No. 314 and known strains

| Medium | | Strain No. 314 | S. lavendulae IFM 1031 | S. racemochromogenes IFM 1081 |
|---|---|---|---|---|
| Sucrose-nitrate agar (Czapek's medium) | VM | abundant, spreading, light olive (1½ ie)* | abundant, spreading, colorless to faint brown | faint brown to purple brown (11 nl) |
| | AM | abundant, white to ivory (2 db) with lavender shade (5 ge to 4 ig) | abundant, white to ivory (2 db) with lavender shade (5 ge to 4 ig) | abundant, ivory (2 dc) to gray (5 dc) |
| | SP | none to faint brown | faint brown | faint brown |
| Glucose-asparagine agar | VM | abundant, spreading, colorless to light olive (1½ ie) | abundant, spreading, grayish blue (10 pn) | abundant, spreading, brown to blue (10 pn) |
| | AM | abundant, grayish pink (5 ec) with lavender shade (5 ge to 4 ig) | abundant, white later becoming to reddish gray with lavender shade (5 ge) | abundant, reddish gray with lavender shade (5 ge) |
| | SP | none to faint brown | none to faint brown | none to faint brown |
| Glycerol-asparagine agar (ISP) | VM | abundant, spreading, colorless | abundant, spreading, dark olive (1½ pn) | dark olive (1½ pn) |
| | AM | moderate, faint brownish gray (2 fe) to silver gray (3 fe) | moderate, faint brownish gray (2 fe) to silver gray (3 fe) | moderate, silver gray (3 fe) |
| | SP | none | light brown | faint olive brown |
| Tyrosine agar | VM | abundant, spreading, faint brown to mustard brown (2 ni) | abundant, spreading, faint brown to mustard brown (2 ni) | abundant, spreading, mustard brown (2 ni) |
| | AM | abundant, reddish gray (7 ge) with lavender shade (5 ge to 4 ig) | abundant, reddish gray (7 ge) with lavender shade (5 ge to 4 ig) | abundant, reddish gray (7 ge) |
| | SP | none to faint brown | none to faint brown | none to faint brown |
| Calcium hydroxy-succinate agar | VM | abundant, spreading, faint brown to dark olive (1 nl) | abundant spreading, bluish brown (3 pn) | abundant, spreading, bluish brown (3 pn) |
| | AM | moderate, thin, powderly, white later becoming to shell tint (3 ba) | none | none |
| | SP | none to faint brown | faint olive brown | faint olive brown |
| Inorganic salts-starch agar | VM | moderate, colorless | moderate, colorless to black olive (2 pn) | dark olive (2 po) |
| | AM | abundant, spreading, yellowish gray (3 dc) | abundant, spreading, yellowish gray (3 dc) | abundant, gray (3 dc), bluish gray (13 ee) |
| | SP | none | none | faint brown |
| Nutrient agar | VM | abundant, spreading, glistening surface, camel (3 ie) | abundant, spreading, glistening surface, camel (3 ie) | abundant, spreading, glistening surface, camel (3 ie) |
| | AM | none | none | none |
| | SP | brown | brown | faint brown |
| Yeast extract-malt extract agar (ISP) | VM | abundant, spreading, much folded, colorless to faint brown | abundant, spreading, colorless to faint brown | folded, faint brown |
| | AM | abundant, grayish pink (5 ec) with lavender shade (5 ge to 4 ig) | abundant, grayish pink (5 ec) with lavender shade (5 ge to 4 ig) | abundant, reddish gray (5 ge) |
| | SP | oak brown (4 pi) | oak brown (4 pi) | dark brown (4 pi) |
| Oatmeal agar (ISP) | VM | moderate, colorless | moderate, dusty blue (15 ni) | bluish brown (15 ni) |
| | AM | moderate, grayish pink (5 ec) with lavender shade (5 ge to 4 ig) | moderate, rose wood with lavender shade (5 ge to 4 ig) | moderate, rose wood (3 ca) |
| | SP | none | none to bluish brown | none to faint brown |
| Egg medium | VM | spreading, much folded, chocolate brown (4 pn) | spreading, much folded, chocolate brown (5 pn) | much folded, chocolate (4 pl) |
| | AM | none | none | poor to none chocolate |
| | SP | faint brown to chocolate brown (4 pl) | faint brown to chocolate brown (4 pl) | |

VM: vegetative mycelium  AM: aerial mycelium  SP: soluble pigment
*Color Harmony Manual code Table 2.

Comparison of physiological properties of Streptomyces strain No. 314 and known strain

| Physiological property | Strain No. 314 | S. lavendulae IFM 1031 | S. racemochromogenes IFM 1081 |
| --- | --- | --- | --- |
| Nitrate reduction (14 days) | + | + | + |
| Liquefaction of gelatin (18° C, 21 days) | + | + | + |
| Soluble pigment | brown | brown | brown |
| Hydrolysis of cellulose (21 days) | − | − | − |
| Litmus milk | | | |
| Coagulation | ++ | ++ | ++ |
| Peptonization | ++ | ++ | ++ |
| pH | 8.0 | 7.8 | 7.8 |
| Melanin formation | + | + | + |

Table 3.

Comparison of carbon source utilization pattern of Streptomyces lavendulae strain No. 314 and known strains

| Carbon source | Strain No. 314 | S. lavendulae IFM 1031 | S. racemochromogenes IFM 1081 |
| --- | --- | --- | --- |
| D-xylose* | − | ± | − |
| L-arabinose* | + | − | − |
| L-rhamnose* | − | − | − |
| D-glucose* | + | + | + |
| D-fructose* | ± | ± | − |
| sucrose* | + | + | + |
| lactose | − | − | + |
| maltose | + | + | + |
| raffinose* | − | − | − |
| mannitol* | − | − | − |
| i-inositol* | − | − | − |
| sodium acetate | + | + | + |
| sodium citrate | + | + | + |
| sodium succinate | + | + | + |
| Control | − | − | − |

*carbon source described in ISP

The chlorocarcin complex and mimosamycin which are produced according to this invention have not yet been isolated from a cultured broth of the aforesaid well-known microorganisms belonging to *Streptomyces lavendulae*.

According to the process of this invention, chlorocarcin complex and mimosamycin are produced by cultivation of *Streptomyces lavendulae* strain No. 314.

Cultivation may be principally conducted according to conventional cultivation procedures of a microorganism, but it is usually favourable to effect submerged culture in a liquid medium. As the medium which may be employed in this invention, there may be any media containing nutrients which the strain No. 314 of the genus Streptomyces may utilize. More specifically, synthetic, semi-synthetic or natural media may be used and, as examples of medium components, there may be mentioned a carbon source, such as glucose, maltose, fructose, xylose, starch, glycerol and the like; a nitrogen source, such as meat extract, peptone, gluten meal, cotton seed oil, soybean meal, corn steep liquor, dry yeast, yeast extract, ammonium sulfate, ammonium chloride, urea and other organic or inorganic nitrogen sources. Carbonates, phosphates or other salts of metals may be additionally incorporated into a medium. In case where an exceeding foaming is observed during cultivation, it is convenient to add to a medium an antifoaming agent, such as a vegetable oil, e.g., soybean oil; silicon oil; polyoxyalkylene type agents; mineral oils and the like.

Cultivation temperature is usually within a range of about 27°–30° C. As a volume of the medium is increased, it is suitable to effect a seed culture and then inoculate the seed culture to a medium. Cultivation period of time is usually from about 18 hours to about 24 hours.

The aforesaid culture conditions may be selected for optimum and applied depending upon the microorganism to be used for production of the present antibiotics.

The antibiotic substances thus accumulated in a cultured broth are usually included within mycelia and culture liquid and extracted from the mycelia collected by centrifugation or filtration and the filtrate thus recovered. More specifically, the present antibiotic substances may be isolated, recovered and purified by conventional procedures commonly employed for the production of a natural product, for instance, those of utilizing solubility and solubility difference in suitable solvents, separability and difference in a separating rate from a solution, difference in adsorption and affinity on various adsorbents, difference in distribution between two liquid phases and the like. These procedures may be applied, if desired, alone or in optional combination therewith or repeatedly. A representative procedure will be set forth below.

After completion of the cultivation, a cultured broth is filtered to separate mycelia from a filtrate. The filtrate is adjusted to pH 8.0 with 10 N sodium hydroxide. The filtrate may be previously concentrated to one-half—one-third volume for better extraction efficiency with a solvent. In the solvent extraction as noted above, basic, water-soluble antibiotics, for example, streptothricin simultaneously produced by the strain No. 314 are left in the filtrate, while chlorocarcin complex, mimosamycin and the like are extracted into the solvent phase. The solvent phase is concentrated to dryness under reduced pressure, the concentrate is dissolved in a small amount of ethyl acetate, the solution is shaken successively with aqueous sodium hydrogencarbonate, sodium carbonate and sodium hydroxide and separated, whereupon acidic substances are transferred into an aqueous phase. The solvent phase is extracted with 1 N hydrochloric acid, adjusted to pH 9–10 with aqueous ammonia and extracted with chloroform. This step is repeated several times and the solvent phase is concentrated to dryness under reduced pressure to give a crude base component containing chlorocarcin complex and mimosamycin. The component is column-chromatographed over silica gel with a mixture of benzene and ethyl acetate to give a fraction predominantly containing chlorocarcin A and, when developed with ethyl acetate, to give a fraction predominantly containing mimosamycin. These fractions are further purified several times by a silica gel chromatography to give chlorocarcin A and mimosamycin as a yellow syrup and a yellow crystals, respectively.

The chromatography column initially eluted is further eluted with a mixture of ethyl acetate and acetone to give a fraction predominantly containing chlorocarcins B and C, the fraction is concentrated to dryness and the concentrate, a mixture of chlorocarcins B and C, is further purified by a silica gel chromatography to give chlorocarcins B and C as yellow powders, respectively.

Mimosamycin

Crude mimosamycin is recrystallized from a mixture of ethyl acetate and ethyl ether to give the pure yellow crystals.

The ethyl acetate layer left after extraction with 1 N hydrochloric acid was concentrated to dryness and the residue was dissolved in a suitable amount of methanol. To the resulting solution was added water in a sufficient amount to provide a water content of 10% by volume. The aqueous solution was extracted with n-hexane to remove impurities of a lower polarity. The extract was concentrated to dryness and the residue was dissolved in ethyl acetate. The so obtained solution was washed successively with 1 N hydrochloric acid and 1 N sodium hydroxide and then concentrated to dryness to afford as a residue crude neutral components. Mimosamycin is also isolated and purified from the components in the same manner as above.

[A] Physico-chemical properties of mimosamycin
1. Color and State: Yellow prism
2. Melting point: 227°–231° C.
3. Elementary analysis: C: 61.51%, H: 4.79%, N: 5.87%
4. Molecular weight (Mass spectrum) 233
5. Empirical formula: $C_{12}H_{11}NO_4$
6. Ultraviolet absorption spectrum (as shown in FIG. 1):

UV $\lambda_{max}^{methanol}$ nm (log $\epsilon$): 230 (shoulder) (4.16) 317 (4.14), 396 (3.56): $\lambda_{min}^{methanol}$ nm (log $\epsilon$): 277 (3.78), 370 (3.53)

Figure 2:
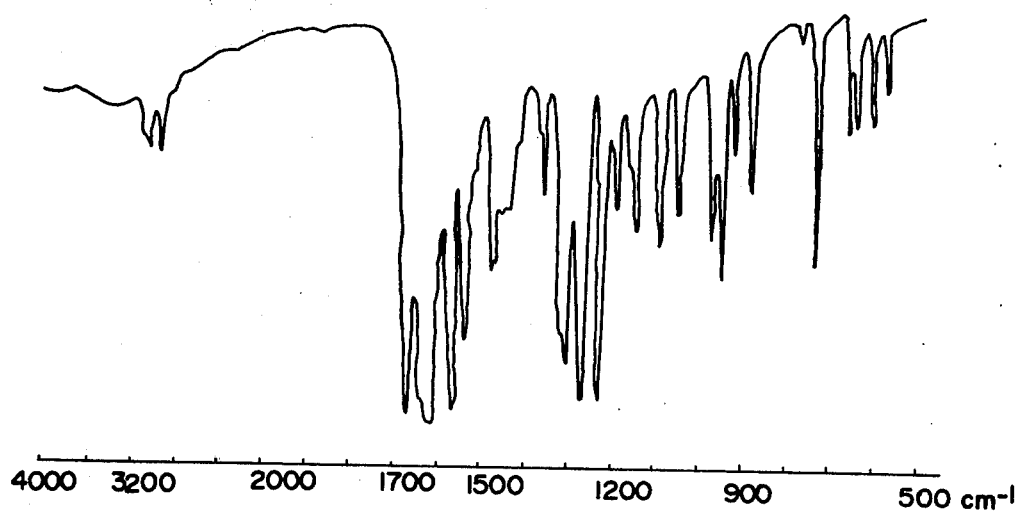

7. Infrared absorption spectrum (as shown in FIG. 2): IR $\nu_{max}^{KBr}$ cm$^{-1}$: 1685, 1655, 1635 1585

Figure 3:
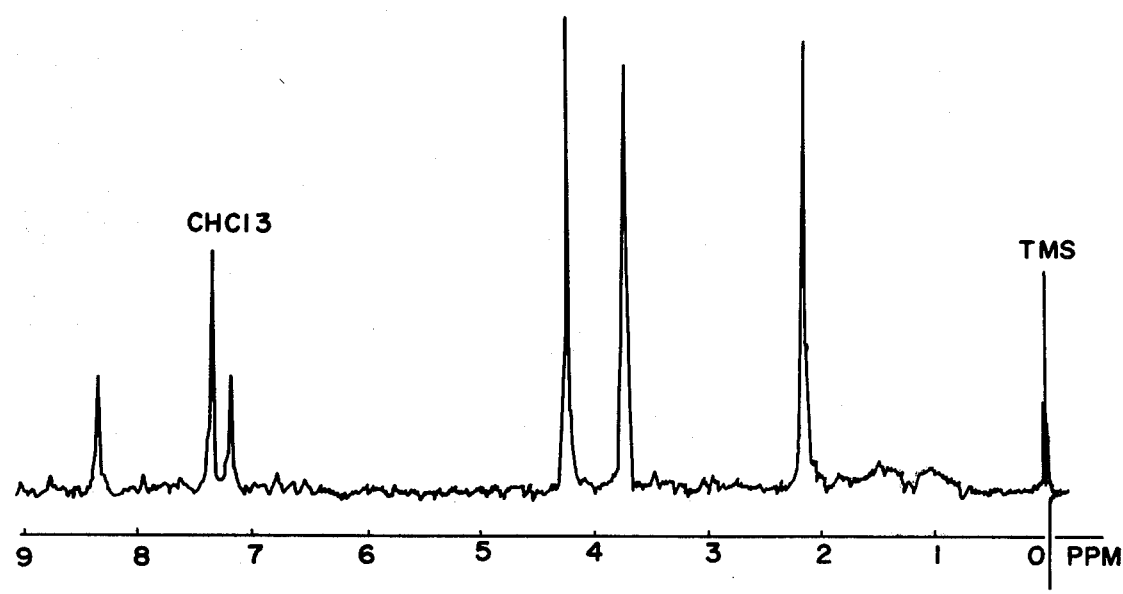

8. NMR spectrum ($CDCl_3$) (as shown in FIG. 3): $\delta$: 2.10 (3H, s.), 3.69 (3H, s.): 4.20 (3H, s.), 7.12 (1H, s.): 8.28 (1H, s.)

9. Rotary dispersion spectrum (C = 4.37 × $10^{-7}$, MeOH)

[$\phi$]$^{20}$ (nm): −1601 (500), −1373 (490),: −1373 (480), −1144 (470), −1144 (460), −1144 (450–390), −1373 (380), −1144 (370–350), −1373 (340), −1831 (330), −2288 (320), −2288 (310), −1831 (300), −1601 (290), −2059 (280), −2517 (270), −3661 (260), −5492 (250), 10. Solubility:
Easily soluble: Methanol, ethanol, chloroform, esters, acetone
Sparingly soluble: Ethyl ether, n-hexane Insoluble: Water 11. Color reaction:
Ehrlich reaction: positive (orange)
Ninhydrin and Dragendorff reaction: negative This substance has biological properties of being active against gram-positive bacteria to a certain extent, but non-effective against gram-negative bacteria and fungi at a concentration of 50 µg/ml.

Especially, the substance is active against acid-fast bacteria and effective against highly streptomycin-resistant strains of human tubercle bacilli as is against normal strains of tubercle bacilli. Minimum inhibitory concentrations for *Mycobacterium tuberculosis* are determined after 4-weeks incubation at 37° C. on Sauton's medium and summarized in Table 4.

Table 4.

| Antimicrobial activity of *mimosamycin* against tubercle bacilli | |
|---|---|
| Test organism | MIC (µg/ml) |
| *Mycobacterium tuberculosis* | |
| H37 R$_V$ | 1.56 |
| *Mycobacterium bovis* No. 10 | 6.25 |
| *Mycobacterium tuberculosis* SMR | 1.56 |
| *Mycobacterium smegmatis* ATCC607 | 25.0 |

Remarks: Nutrient agar, 37° C., 48 hours for *M. smegmatis*. Sauton's liquid medium, 37° C., 4 weeks for other 3 strains. The strains SMR and Matsudo resistant to streptomycin at 1000 µg/ml or higher.

Mice (18–20 g.) tolerated intravenous injection of 50 mg./kg. of mimosamycin.

It has been proved from the above physico-chemical and biological properties that this substance is a new antibiotic substance specifically effective against tubercle bacilli.

Mimosamycin may be employed for therapeutic purpose as an antimicrobial or antituberculous agent in various pharmaceutical preparation forms, such as a tablet, a powder, an oral suspension or syrup, a capsule, a solution or suspension for injection and so on. These forms may be easily prepared by the use of the antibiotic in a conventional manner. The antibiotic may be given via oral or parenteral routes, typically in intramuscular or intravenous injection. The dosage to be administered may vary under any given conditions, but in general will depend upon the severity of the disease and the age and body weight of the patient and so on. Usually, a daily dose is within a range between 200 mg. and 2 g. for adults and may be given in single or multiple doses.

Chlorocarcins A, B and C

Chlorocarcins A, B and C are all basic antibiotic substances and capable of forming the corresponding acid addition salts. Typical examples of such salts are those with such inorganic or organic acids as hydrochloric acid, sulfuric acid, phosphoric acid, stearic acid, propionic acid, tartaric acid, maleic acid and the like. As is expected, this sort of salts also show the same level of an antibiotic activity as the free antibiotic substances do, although some differences in their activities and solubilities are usually observed.

Physico-chemical properties of chlorocarcins A, B and C are given below.

Figure 4:
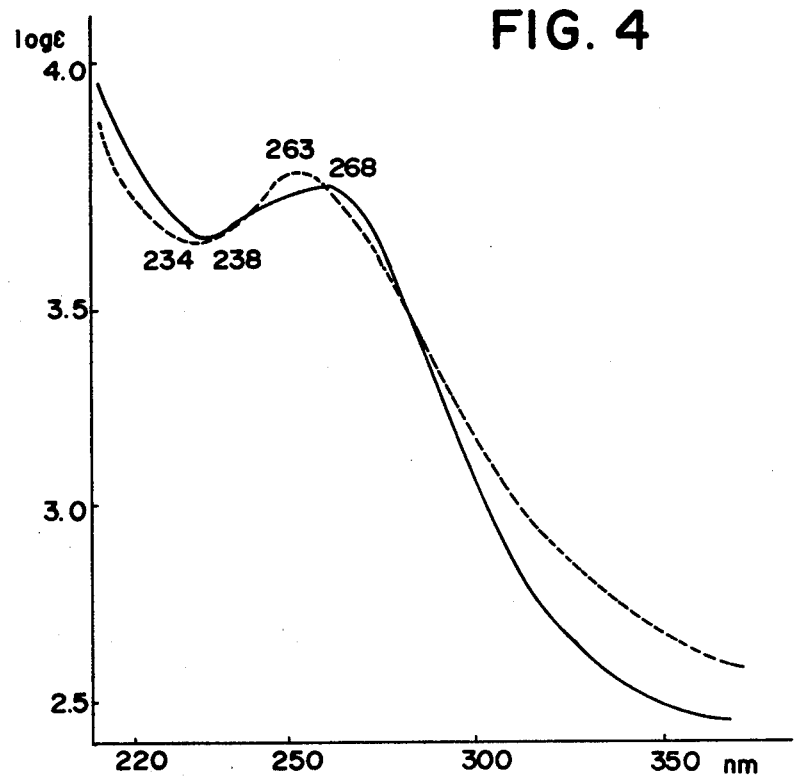

[B] Physico-chemical properties of chlorocarcin A
1. Color and State: Yellow syrup (free base)
2. Melting point: 140°–144° C. (HCl salt, decomp.):
3. Elementary analysis (as HCl salt): C: 45.74%, H: 4.73%, N: 6.94%, Cl: 16.14%
4. Molecular weight (Mass spectrum): 535
5. Empirical formula: $C_{24}H_{26}N_3O_9Cl.2HCl \cdot H_2O$
6. Specific rotation: $[\alpha]_D^{28} = -4°$ (C = 1.0, methanol)
7. Ultraviolet absorption spectrum (as shown in FIG. 4 wherein full and dotted lines show UV spectra in MeOH and 0.1N HCl-MeOH, respectively)

UV $\lambda_{max}^{methanol}$ nm (log $\epsilon$) = 268 (3.83)
$\lambda_{min}^{methanol}$ nm (log $\epsilon$) = 238 (3.68)
$\lambda_{max}^{0.1N\ HCl-MeOH}$ nm (log $\epsilon$) = 263 (3.85)
$\lambda_{min}^{0.1N\ HCl-MeOH}$ nm (log $\epsilon$) = 234 (3.68)

Figure 5:
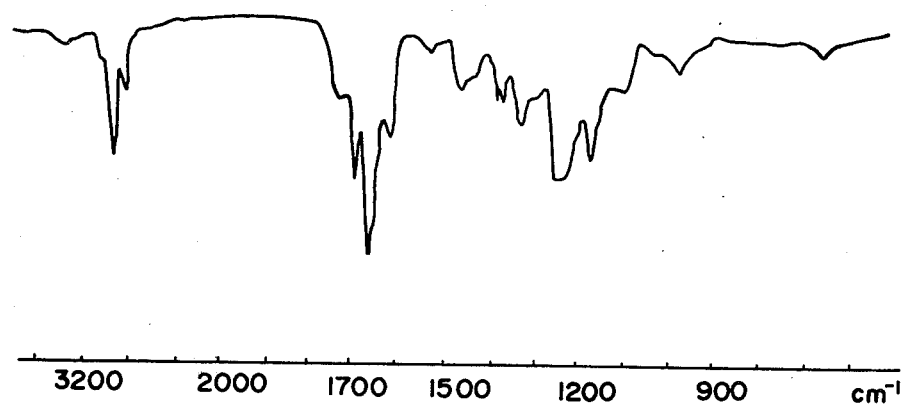

8. Infrared absorption spectrum (as shown in FIG. 5) IR $\nu_{max}^{CHCl_3}$ cm$^{-1}$: 1685, 1665, 1610

Figure 6:
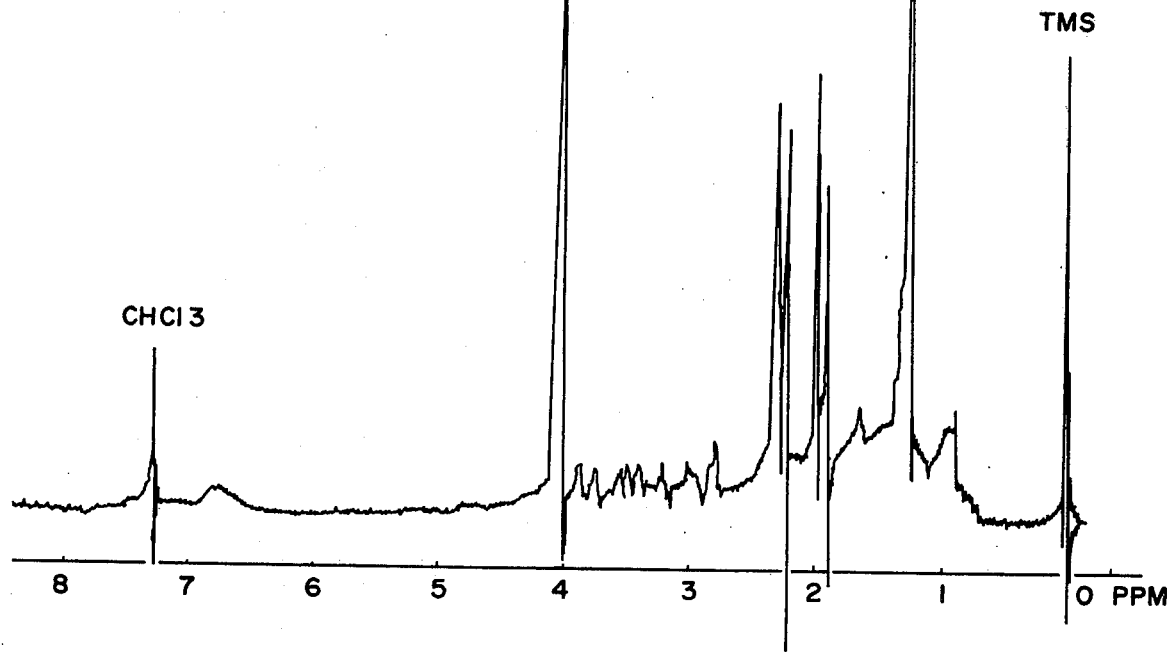

9. NMR ($CDCl_3$) (as shown in FIG. 6):
$\delta$: 1.23 (3H, s.)
1.95 (3H, s., J=7Hz)

2.26 (3H, d., J=7Hz)
4.05 (3H, s.)
6.70 (1N, s.)

10. Solubility: Easily soluble: Ethyl ether, esters, chloroform, acetone, alcohols, 0.1N HCl Sparingly soluble: n-hexane, 0.1N NaOH Insoluble: Water 11. Color reaction Dragendorff reaction: positive Ninhydrin, FeCl$_3$ and anthrone reactions: negative

[C] Physico-chemical properties of chlorocarcin B free base

Figure 7:
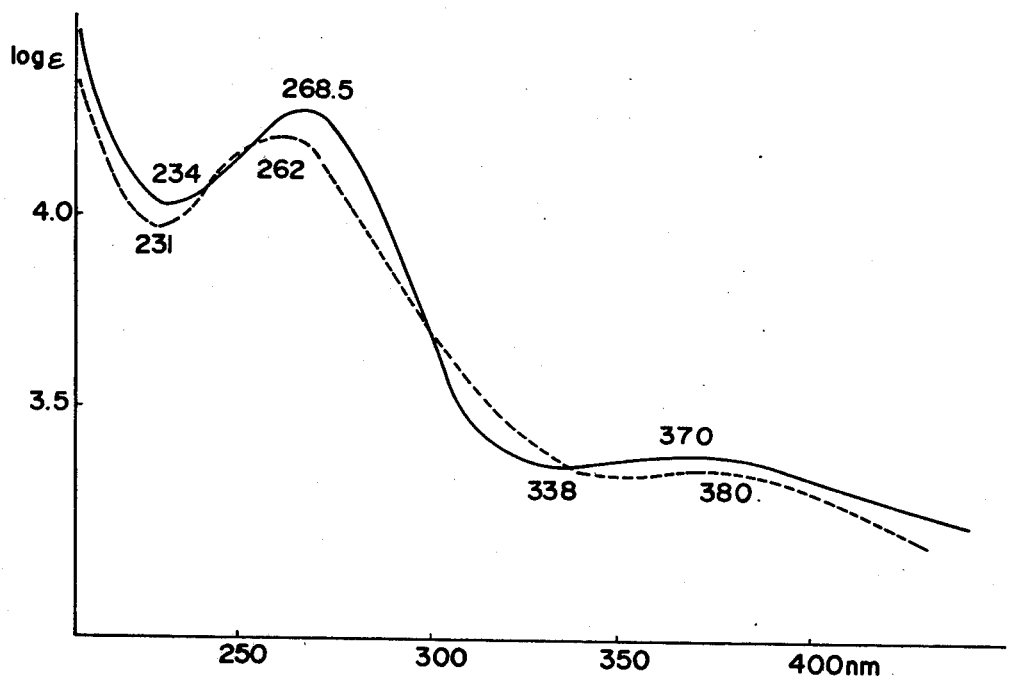

1. Color and state: Yellow powder
2. Melting point: 78°–81° C.
3. Elementary analysis C: 60.89%, H: 6.20%, N: 6.71%, Cl: 5.20%
4. Molecular weight (Mass spectrum) 553
5. Empirical formula: $C_{29}H_{32}O_6N_3Cl \cdot 5/4\ H_2O$
6. Ultraviolet absorption spectrum (as shown in FIG. 7 wherein full and dotted lines shown UV spectra in MeOH and 0.1N HCl-MeOH, respectively)

UV $\lambda_{max}^{methanol}$ nm (log ε): 268.5 (4.25), 370 (3.38):
$\lambda_{min}^{methanol}$ nm (log ε): 234 (3.99), 338 (3.34):
$\lambda_{max}^{0.1N\ HCl-MeOH}$ nm (log ε): 262 (4.18), 380 (3.34):
$\lambda_{min}^{0.1N\ HCl-MeOH}$ nm (log ε): 231 (3.95), 354 (3.32)

Figure 8:
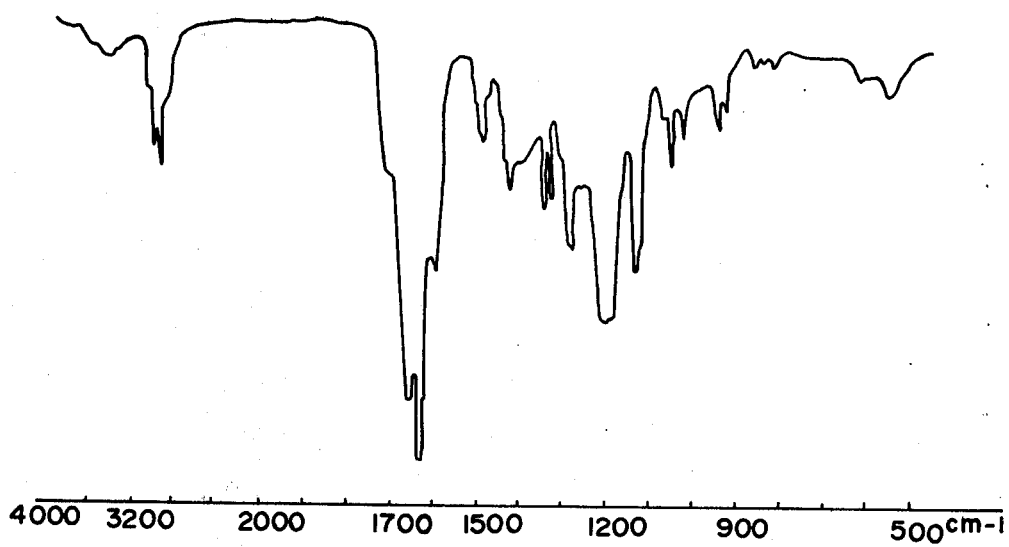

7. Infrared absorption spectrum (as shown in FIG. 8) IR $\nu_{max}^{CHCl_3}$ cm$^{-1}$: 1715, 1683, 1655, 1612

Figure 9:
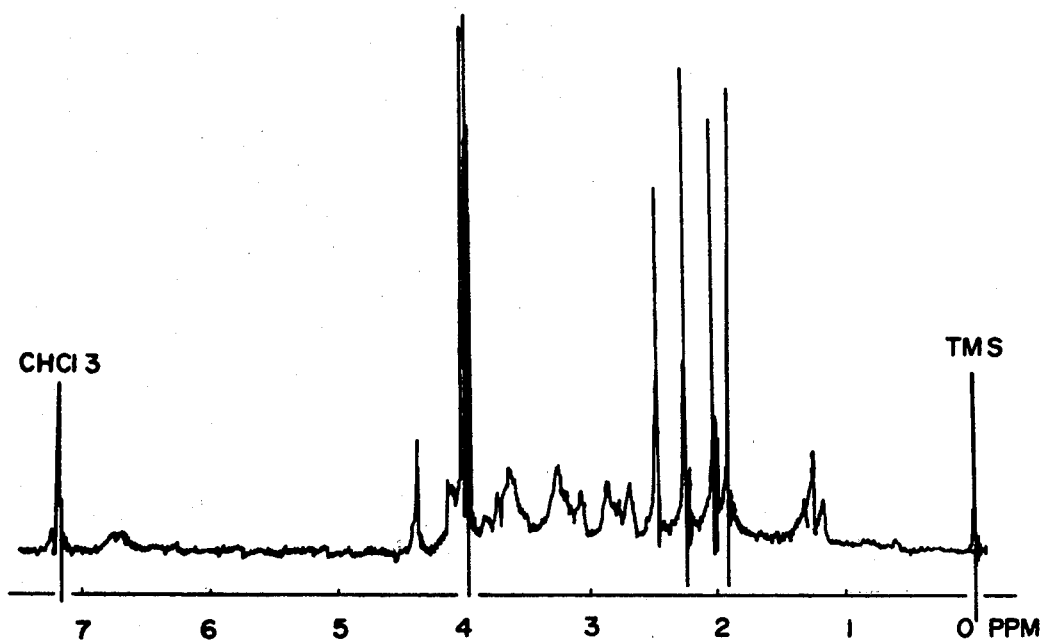

8. NMR spectrum (CDCl$_3$) (as shown in FIG. 9) δ: 1.28 (3H, m.), 1.92 (3H, s.), 2.04 (3H, s.), 2.27 (3H, s.), 2.50 (3H, s.), 4.04 (3H, s.), 4.08 (3H, s.), 4.42 (1H, s.), 6.84 (1H, d., J = 8Hz)

9. Circular dichroism spectrum (C = 8.63 × 10$^{-5}$, methanol): Δε (nm) : −2.45 (360) (negative maximum) : −0.352 (320L) (positive maximum): −13.0 (2.78) (negative maximum)

10. Solubility:
Easily soluble: Lower alcohols, chloroform, esters, acetone, benzene, ethyl ether Sparingly soluble: n-hexane Insoluble: Water 11. Color reaction: Dragendorff and Meyer reactions: positive Ninhydrin and Ehrlich reactions: negative

[D] Physico-chemical properties of chlorocarcin C

Figure 10:
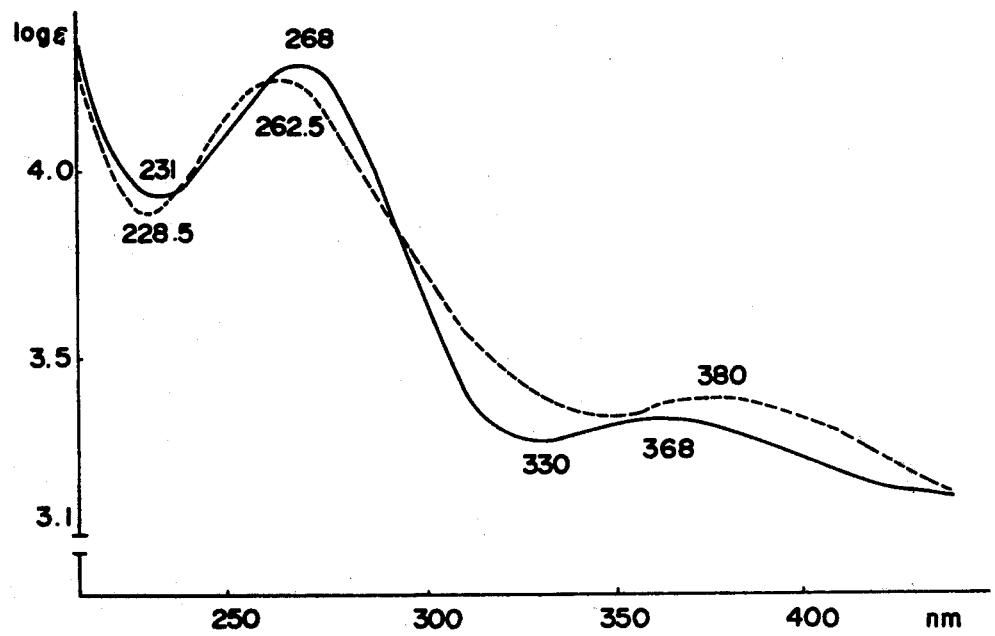

1. Color and state: Yellow powder
2. Melting point 79°–84° C.
3. Elementary analysis: C: 60.88%, H: 6.11%, N: 6.54%, Cl: 6.71%
4. Molecular weight (Mass spectrum): 567
5. Empirical formula: $C_{30}H_{34}O_6N_3Cl \cdot 3/2\ H_2O$
6. Ultraviolet absorption spectrum (as shown in FIG. 10 wherein full and dotted lines show UV spectra in MeOH and 0.1N HCl-MeOH, respectively)

UV $\lambda_{max}^{Methanol}$ nm (log ε): 268 (4.26), 368 (3.34)
$\lambda_{min}^{methanol}$ nm (log ε): 231 (3.91)
$\lambda_{max}^{0.1N\ HCl-MeOH}$ nm (log ε): 262.5 (4.22), 380 (3.40)
$\lambda_{min}^{0.1N\ HCl-MeOH}$ nm (log ε): 228.5 (3,87), 351 (3.36)

Figure 11:
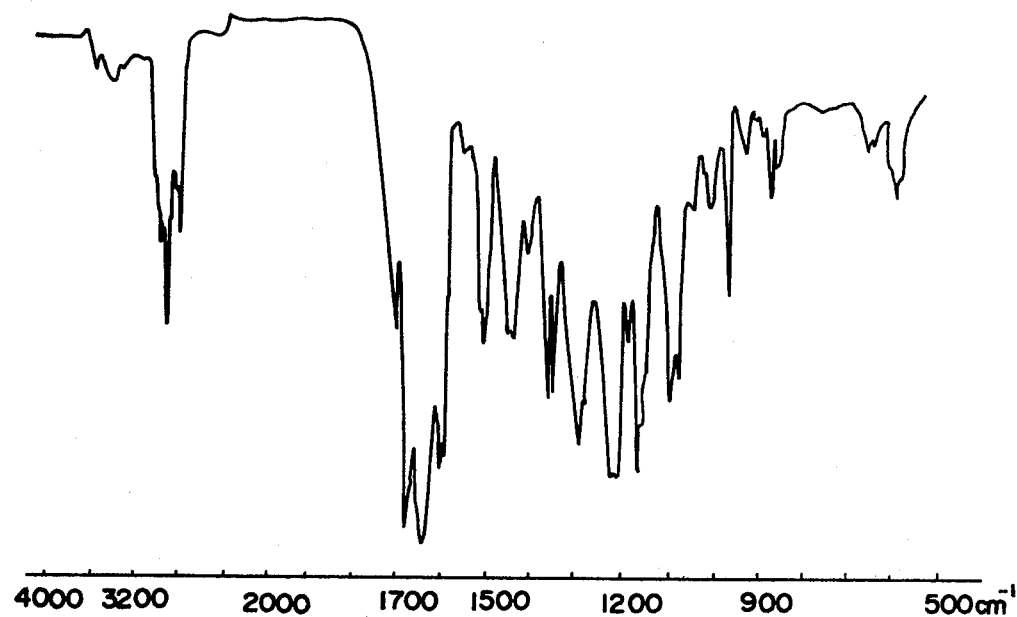

7. Infrared absorption spectrum (as shown in FIG. 11): IR $\nu_{max}^{CHCl_3}$ cm$^{-1}$: 1718, 1683, 1655, 1618

8. NMR spectrum (FIG. 12): δ: 1.42 (3H, s.), 2.01 (3H, s.), 2.15 (3H, s.), 2.35 (3H, s.), 2.59 (3H, s.), 3.59 (3H, s.), 4.05 (3H, s.), 4.07 (3H, s.), 6.71 (1H, d., J=8H$_z$)

9. Circular dichroism spectrum: (C = 9.38 × 10$^{-5}$, methanol): Δε (nm): −3.88 (360) (negative maximum)
: −2.26 (310) (positive maximum)
: −24.5 (273) (negtive maximum)

10. Solubility: Easily soluble: Lower alcohols, chloroform, esters, acetone, benzene, ethyl ether Sparingly soluble: n-hexane Insoluble: Water 11. Color reaction: Dragendorff and Meyer reactions: positive Ninhydrin and Ehrlich reactions: negative Chlorocarcins A, B and C possess an antibacterial activity and they are utilizable as medicines. Antimicrobial spectra of chlorocarcins A, B and C are summarized in Table 5 wherein the antibiotics mainly show an antibacterial activity against gram-positive bacteria but do little antibacterial activity against most gram-negative bacteria. and C show cytostatic activities against L 1210 mouse Table 5
Antimicrobial spectra of chlorocarcins A, B and C

| Test organism | MIC (μg/ml) | | |
|---|---|---|---|
| | Chlorocarcin A | Chlorocarcin B | Chlorocarcin C |
| Staphylococcus aureus 209 P | 0.1 | 12.5 | 12.5 |
| Staphylococcus aureus Smith | 0.02 | 12.5 | 12.5 |
| Staphylococcus albus | 0.1 | 50 | 50 |
| Staphylococcus citreus | 0.1 | 25 | 25 |
| Streptococcus hemolyticus Coock | 6.25 | 6.25 | 6.25 |
| Streptococcus hemolyticus 090R | 50 | 100 | 100 |
| Streptococcus salivarius | 6.25 | 50 | 50 |
| Streptococcus faecalis | 25 | >100 | >100 |
| Bacillus subtilis PCI 219 | 0.2 | 25 | 25 |
| Bacillus cereus | 50 | 50 | 50 |
| Corynebacterium diphtheriae | 0.003 | 0.05 | 0.05 |
| Corynebacterium xerosis | 0.003 | 0.39 | 0.39 |
| Lactobacillus arabinosus | 12.5 | 50 | 50 |
| Nocardia asteoides | 25 | 50 | 50 |
| Mycobacterium smegmatis ATCC 607 | 100 | >100 | >100 |
| Mycobacterium phlei | 100 | >100 | >100 |
| Mycobacterium avium | 100 | >100 | >100 |
| Escherichia coli | >100 | >100 | >100 |
| Shigella dysenteriae | >100 | >100 | >100 |
| Salmonella typhimurium | >100 | >100 | >100 |
| Klebsiella pneumoniae | 100 | 50 | 50 |
| Serratia marcescens | >100 | >100 | >100 |
| Pseudomonas aeruginosa | >100 | >100 | >100 |
| Brucella abortus | >100 | >100 | >100 |
| Candida albicans | >100 | >100 | >100 |
| Saccharomyces cerevisiae | >100 | >100 | >100 |
| Tolura rubra | >100 | >100 | >100 |
| Penicillium glaucum | >100 | >100 | >100 |
| Aspergillus niger | >100 | >100 | >100 |
| Aspergillus oryzae | >100 | >100 | >100 |
| Mucor mucedo | >100 | >100 | >100 |
| Trichophyton mentagrophytes | 100 | >100 | >100 |

Medium and Culture Condition: 1% glucose nutrient agar (3% glycerin nutrient agar for acid-fast bacteria, blood agar for *Streptococcus hemolyticus* and *Brucella abortus*), 37° C., 24 or 48 hours. Sabouraud.dextrose.a- gar for fungi, 27° C., 48 hours (72 hours for *Trichophyton mentagrophytes*).

Chlorocarcins A, B and C are of a relatively low toxicity and tolerable in mice, average body weight of 18–20 g., via intravenous injection at 25 mg./kg. (A) and 250 mg./kg. (B and C), respectively.

Antibacterial activities during cultivation and extraction procedures are assayed by an agar plate disc method using *Bacillus subtilis* PCI 219. Assay of streptothricin is conducted using *Escherichia coli* strain $F_1$, as the strain No. 314 can produce said antibiotic in a large amount. Co-existence of streptothricin can be easily decided by determination of an antibacterial activity against *E. coli*, as the chlorocarcin complex, namely the fraction extracted into a solvent, has no activity against *E. coli*. 1 Mimosamycin is similarly assayed using as test organism *Mycobacterium smegmatis* ATCC 607.

The estimated effective dosage of chlorocarcin A appears to be within 10 mg. to 1 g. daily for adults and the dosage of chlorocarcins B and C will be 100 mg.-10 g. daily. Chlorocarcins may be administered in similar pharmaceutical preparations to those set forth about mimosamycin and advantageously via parenteral and, in some cases, oral routes, usually intramuscularly or intravenously.

Particular embodiment of the production of the present antibiotic substances as depicted above will be more fully illustrated by the following examples.

EXAMPLE 1.

Shaking culture in flasks

A. Seed Culture

A suspension of a freeze-dried preparation of *Streptomyces lavendulae* strain No. 314 in physiological saline was prepared and inoculated on agar slant having the following composition.

| Glucose | 10 | g |
|---|---|---|
| L-asparagine | 5 | g |
| $KH_2PO_4$ | 5 | g |
| Agar | 15 | g |
| Tap water | 1000 | ml |
| pH | 6.8 – 7.0 | |

Cultivation was continued at 27° C. for 1 week to afford a seed culture with abundant growth and many spores. B. Culture One hundred shaking flasks, each being of 500 ml-volume and containing 100 ml of the culture medium as defined below, were aseptically inoculated with the spores collected from the above seed culture in two loopfuls per flask.

| Glucose | 1.0 | g |
|---|---|---|
| Starch | 10.0 | g |
| Polypepton (available from Wako Pure Chemical Industries, Ltd., Japan) | 10.0 | g |
| Meat extract (") | 5.0 | g |
| NaCl | 3.0 | g |
| Silicone KM 72 (Shin-Etsu Chemical Co., Ltd., Japan) | 10 | ml |
| Tap water | 1000 | ml |
| pH | 7.0 | |

Cultivation was effected at 27° C. for 40 hours by means of a reciprocal shaking apparatus (125 strokes) per minute, 8 cm vibration).

After completion of the cultivation, contents of the flasks were combined and mycelia were removed by means of a continuous centrifugal separator. The supernatant portion (10 *l*) thus obtained was adjusted to pH 8.0 and then extracted three times with one-third volume of chloroform.

The extracts were combined, filtered through a filter paper and then concentrated to dryness under reduced pressure to give 2.8 g. of a dark brown solid substance. A solution of the substance in 50 ml of ethyl acetate was shaken successively with 5% aqueous sodium hydrogencarbonate, 1 N sodium carbonate and 1 N sodium hydroxide in each 25 ml portion to remove acidic substances. The organic layer was extracted five times with 25 ml of 1 N hydrochloric acid. The extracts were combined with the aqueous layer and the mixture was adjusted to pH 9–10 with aqueous ammonia and extracted five times with an equal volume of chloroform. The extracts were combined and concentrated to dryness. The residue was dissolved in 50 ml of a 10% aqueous solution of acetic acid and adjusted to pH 9–10 with aqueous ammonia and extracted five times with an equal amount of chloroform. The extract was concentrated under reduced pressure to give 200 mg. of a crude extract containing chlorocarcin complex and mimosamycin.

The crude extract thus obtained was charged into a glass column (diameter of 1.0 cm and length of 50 cm) packed with silica gel (70–230 mesh, available from Merck & Co., U.S.A.). The column was developed with mixtures of benzene: ethyl acetate (2:1), (1:1), (1:2) to give fractions predominantly containing chlorocarcin A and mimosamycin. Each fraction was further chromatographed with a silica gel (230 mesh, available from Merck & Co.) column to give 5.2 mg. of chlorocarcin A as a yellow powder and 2.8 mg. of mimosamycin as yellow crystals.

The initial column was further developed with ethyl acetate:acetone (1:1) to give fractions (73 mg.) containing chlorocarcins B and C. The fraction thus obtained was repeatedly chromatographed with a silica gel column (230 mesh, available from Merck & Co.) using acetone as a developing solvent to give 28 mg of chlorocarcin B and 7.3 mg of chlorocarcin C.

EXAMPLE 2

Culture in jar fermenters

A. A seed culture was prepared in the same manner as in Example 1 except that cultivation was effected for 24 hours.

B. Four jar fermenters, each being of 20 *l*-volume and containing 15 *l* of the culture medium as defined below, were sterilized under pressure in a conventional manner.

| Glucose | 5.0 | g |
|---|---|---|
| Starch | 5.0 | g |
| Polypepton (available from Wako Pure Chemical Industries, Ltd., Japan) | 10.0 | g |
| Meat extract (") | 5.0 | g |
| NaCl | 3.0 | g |
| Tap water | 1000 | ml |
| pH | 7.0 – 7.2 | |

Cultivation was continued for 18 hours under the following condition.

| | |
|---|---|
| Seed culture | 1% |
| Cultivation temperature | 27° C |
| Agitation | 550 rpm |
| Flow rate of aseptic air | 1 volume of medium per min. |
| Antifoaming agent (Silicon KM 72) | Added, if necessary |

After the lapse of the above time, the maximum titers of the produced chlorocarcin complex and mimosamycin were obtained and thereafter the titers rapidly decreased. The pH of a cultured broth fell below 6.0 and thereafter again rose to approximately 6.8. Mycelium volume rapidly increased and the glucose was almost exhausted at that time. At the maximum titer of chlorocarcin, a dilution method using *Bacillus subtilis* PCI 219 as test organism showed 512 dilution unit and an agar plate diffusion method showed an inhibition zone of about 40 mm. The maximum production of streptothricin was achieved in about 30 hours. From the cultured broth (about 60 *l*) pooled from the jar fermenters were removed mycelia by means of a continuous centrifugal separator and the culture liquid was concentrated to one-third volume.

The concentrate was adjusted to pH 8.0 with 1 N sodium hydroxide and extracted three times with an equal volume of chloroform. The extracts were combined and concentrated under reduced pressure to give 16.4 g. of a mixture of crude chlorocarcin complex and mimosamycin. The mixture was dissolved in 100 ml of ethyl acetate and the solution was washed with 50 ml of 5% aqueous sodium hydrogencarbonate and 1 N sodium carbonate and then four times with 1 N sodium hydroxide while stirring. The sodium hydroxide layer contained acidic inactive components, particularly stearic acid. The ethyl acetate layer was shaken five times with 60 ml of 1 N hydrochloric acid, whereupon basic substances were extracted into the acid. The acid extracts were combined, adjusted to pH 9–10 with aqueous ammonia, extracted five times with an equal volume of chloroform and the organic layer was separated and concentrated under reduced pressure to give crude basic substances. The substances were dissolved in 60 ml of a 10% aqueous solution of acetic acid and the solution was again adjusted to pH 9–10 with aqueous ammonia, extracted five times with an equal volume of chloroform. The extracts were combined and concentrated under reduced pressure to give about 0.98 g. of crude product containing chlorocarcin complex and mimosamycin.

A total amount of the crude product from 4 jar fermenters was about 0.2–1.5 g.

Cultivation was repeated 140 times using 4 jar fermenters and a total amount of cultured broth of 840 *l* to give 8.67 g. of the crude product.

The crude product dissolved in a small amount of benzene was charged into a glass column with a diameter of 5 cm which was packed with benzene-soaked silica gel (70–230 mesh, Merck & Co.). The column was developed with benzene: ethyl acetate (2:1). After contaminants were eluted, fraction mainly containing chlorocarcin A and that mainly containing mimosamycin were successively eluted with the same developing solvent, respectively. These fractions were concentrated and chromatographed over silica gel (230 mesh, Merck & Co.) to give 42 mg. of mimosamycin and 85 mg. of chlorocarcin A.

The initial column was eluted with ethyl acetate: acetone (1:1) to give a mixture of chlorocarcins B and C. The mixture was repeatedly chromatographed using silica gel (230 mesh, Merck & Co.) and the same solvent to give 215 mg. of chlorocarcin B and 52 mg. of chlorocarcin C in a pure state, respectively.

Figure 12:
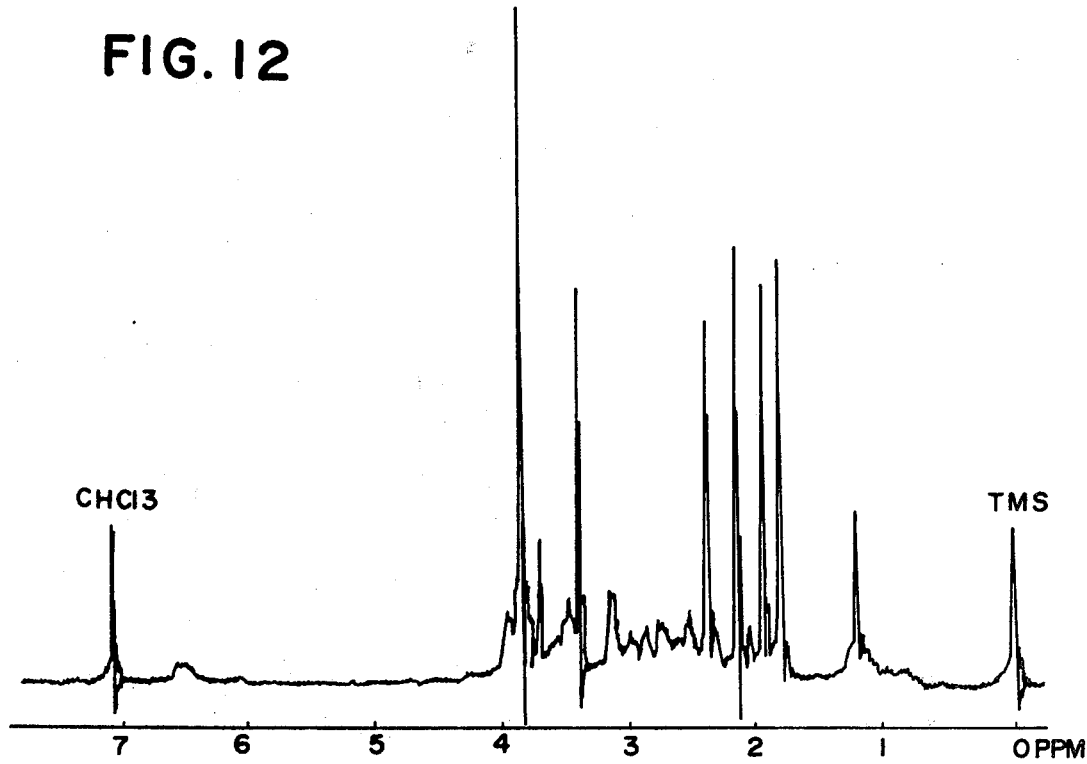

What is claimed is:

1. A process for the production of antibiotic substances selected from the group consisting of mimosamycin and chlorocarcin A, chlorocarcin B and Chlorocarcin C and acid addition salts thereof, which comprises cultivating Streptomyces lavendulae strain No. 314, recovering a complex of chlorocarcins and mimosamycin from a cultured broth and then isolating mimosamycin and chlorocarcins A, B and C from said complex, wherein mimosamycin is a neutral yellow prism form which has a melting point of 227°–231° C.; a composition of 61.51% carbon, 4.79% hydrogen and 5.8% nitrogen; a molecular weight of 233 according to mass spectrum; an empirical formula of $C_{12}H_{11}NO_4$; an ultraviolet absorption spectrum shown in FIG. 1, UV $\lambda_{max}^{MeOH}$ nm (log $\epsilon$): 230 (shoulder (4.16), 317 (4.14), 396 (3.56), UV $\lambda_{min}^{MeOH}$ nm (log $\epsilon$): 277 (3.78), 370 (3.53); an infrared absorption spectrum shown in FIG. 2, IR $\nu_{max}^{KBr}$ cm$^{-1}$: 1685, 1655, 1635, 1585; an NMR spectrum (CDCl$_3$) shown in FIG. 3, $\delta$: 2.10 (3H, s.), 3.69 (3H, s.), 4.20 (3H, s.), 7.12 (1H, s.), 8.28 (1H, s.); a rotary dispersion spectrum (C = 4.37 × 10$^{-7}$, MeOH) of [$\phi$]$^{20}$ (nm): −1601 (500), −1373 (490), −1373 (480), −1144 (470), −1144 (460), −1144 (450 − 390), −1373 (380), −1144 (370 − 350), −1373 (340), −1831 (330, −2288 (320), −2288 (310), −1831 (300), −1601 (290), −2059 (280), −2517 (270), −3661 (260), −5492 (250); and is easily soluble in methanol, ethanol, chloroform, an ester and acetone, sparingly soluble in ethyl ether and n-hexane and insoluble in water; and positive to Ehrlich reagent and negative to ninhydrin and Dragendorff reagent;

chlorocarcin A is a basic yellow syrup form which has a melting point of 140°–144° C. (decomp., as its HCl salt form); a composition (as its HCl salt form) of 45.74% carbon, 4.73% hydrogen, 6.94% nitrogen and 16.14% chlorine, a molecular weight of 535 according to mass spectrum; an empirical formula of $C_{24}H_{26}N_3O_9Cl \cdot 2HCl \cdot H_2O$; a specific rotation of $[\alpha]_D^{28} = -4°$ ($c = 1.0$, methanol); an ultraviolet absorption spectrum shown in FIG. 4, UV $\lambda_{max}^{MeOH}$ nm (log $\epsilon$): 268 (3.83), UV $\lambda_{min}^{MeOH}$ nm (log $\epsilon$): 238 (3.68), UV $\lambda_{max}^{0.1N\ HCl\text{-}MeOH}$ nm (log $\epsilon$): 263 (3.85), UV $\lambda_{min}^{MeOH\text{-}0.1N\ HCl}$ nm (log $\epsilon$): 234 (3.68); an infrared absorption spectrum shown in FIG. 5, IR $\nu_{max}^{CHCl_3}$ cm$^{-1}$: 1685, 1665, 1610; an NMR spectrum (CDCl$^3$) shown in FIG. 6, $\delta$: 1.23 (3H, s.), 1.95, (3H, s., J=7 H$_z$), 2.26 (3H, s., J=7 H$_z$), 4.05 (3H, s.), 6.70 (1H, s.) and is easily soluble in ethyl ether, an ester, chloroform, acetone, an alcohol and 0.1 N HCl, sparingly soluble in n-hexane and 0.1 N NaOH and insoluble in water and positive to Dragendorff reagent and negative to ninhydrin, FeCl$_3$ and anthrone reagents, and a pharmaceutical acid addition salt thereof;

chlorocarcin B is a basic yellow powder form which has a melting point of 78°–81° C.; a composition of 60.89% carbon, 6.20% hydrogen, 6.71% nitrogen and 5.20% chlorine; a molecular weight of 553 according to mass spectrum; an empirical formula of $C_{29}H_{32}O_6N_3Cl \cdot 5/4\ H_2O$; an ultraviolet absorption spectrum shown in FIG. 7, UV $\lambda_{max}^{MeOH}$ nm (log ε): 268.5 (4.25), 370 (3.38), UV $\lambda_{min}^{MeOH}$ nm (log ε): 234 (3.99), 338 (3.34), UV $\lambda_{max}^{0.1N\ HCl-MeOH}$ nm (log ε): 262 (4.18), 380 (3.34), UV $\lambda_{min}^{0.1N\ HCl-MeOH}$ nm (log ε): 231 (3.95), 354 (3.32); an infrared absorption spectrum shown in FIG. 8, IR $\nu_{max}^{CHCl_3}$ cm$^{-1}$: 1715, 1683, 1655, 1612; an NMR spectrum (CDCl$_3$) shown in FIG. 9, δ: 1.28 (3H, m.), 1.92 (3H, s.), 2.04 (3H, s.), 2.27 (3H, s.), 2.50 (3H, s.), 4.04 (3H, s.), 4.08 (3H, s.), 4.42 (1H, s.), 6.84 (1H, d., J=8H$_z$); a circular dichroism spectrum (C = 9.63 × 10$^{-5}$, methanol), Δε(nm): −2.45 (360) (negative maximum): −0.352 (320) (positive maximum): −13.0 (2.78) (negative maximum); and is easily soluble in an alcohol, chloroform, an ester, acetone, benzene and ethyl ether, sparingly soluble in n-hexane and insoluble in water and positive to Dragendorff and Meyer reagents and negative to ninhydrin and Ehrlich reagents, and a pharmaceutical acid addition salt thereof; and chlorocarcin C is a basic yellow powder form which has a melting point of 79°–84° C.; a composition of 60.88% carbon, 6.11% hydrogen, 6.54% nitrogen and 6.71% chlorine; a molecular weight of 567 according to mass spectrum; an empirical formula of $C_{30}H_{34}O_6N_3Cl.3/2\ H_2O$; an ultraviolet absorption spectrum shown in FIG. 10, UV $\lambda_{max}^{MeOH}$ nm (log ε): 268 (4.26), 368 (3.34), UV $\lambda_{min}^{MeOH}$ nm (log ε): 231 (3.91), UV $\lambda_{max}^{0.1N\ HCl-MeOH}$ nm (log ε): 262.5 (4.22), 380 (3.40), UV $\lambda_{min}^{0.1N\ HCl-MeOH}$ nm (log ε): 228.5 (3.87), 351 (3.36); an infrared absorption spectrum shown in FIG. 11, IR $\nu_{max}^{CHCl_3}$ cm$^{-1}$: 1718, 1683, 1655, 1618; an NMR spectrum shown in FIG. 12; : 1.42 (3H, s.), 2.01 (3H, s.), 2.15 (3H, s.), 2.35 (3H, s.), 2.59 (3H, s.), 3.59 (3H, s.), 4.05 (3H, s.), 4.07 (3H, s.), 6.71 (1H, d., J = 8H$_z$); a circular dichroism spectrum (C = 9.38 × 10$^{-5}$, methanol), Δε(nm): −3.88 (360) (negative maximum): −2.26 (310) (positive maximum): −24.5 (273) (negative maximum); and is easily soluble in an alcohol chloroform, an ester, acetone, benzene and ethyl ether, sparingly soluble in n-hexane and insoluble in water, and a pharmaceutical acid addition salt thereof.

2. A process according to claim 1 wherein submerged culture is effected in a liquid medium.

3. A process according to claim 1 wherein cultivation is effected at a temperature between 27° C. and 30° C.

* * * * *